US009924916B2

(12) United States Patent
Kato et al.

(10) Patent No.: US 9,924,916 B2
(45) Date of Patent: Mar. 27, 2018

(54) X-RAY CT APPARATUS AND CONTROLLING METHOD

(71) Applicant: Toshiba Medical Systems Corporation, Otawara-shi (JP)

(72) Inventors: Tooru Kato, Nasushiobara (JP); Hiroaki Nakai, Nasushiobara (JP); Kanta Kobuchi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 200 days.

(21) Appl. No.: 14/744,082

(22) Filed: Jun. 19, 2015

(65) Prior Publication Data

US 2015/0282778 A1    Oct. 8, 2015

Related U.S. Application Data

(63) Continuation of application No. PCT/JP2013/085131, filed on Dec. 27, 2013.

(30) Foreign Application Priority Data

Dec. 27, 2012   (JP) ................................. 2012-285234

(51) Int. Cl.
*A61B 6/03*    (2006.01)
*A61B 6/00*    (2006.01)
*G06T 11/00*   (2006.01)

(52) U.S. Cl.
CPC ............... *A61B 6/482* (2013.01); *A61B 6/42* (2013.01); *A61B 6/4208* (2013.01);
(Continued)

(58) Field of Classification Search
CPC ......... A61B 6/032; A61B 6/42; A61B 6/4208; A61B 6/4233; A61B 6/4241; A61B 6/482; A61B 6/54; A61B 6/542; A61B 6/545
(Continued)

(56) References Cited

U.S. PATENT DOCUMENTS 5,155,365 A * 10/1992 Cann .................... A61B 6/4241
                                              250/363.02
5,379,333 A *  1/1995 Toth ...................... A61B 6/032
                                              378/108
(Continued)

FOREIGN PATENT DOCUMENTS

CN   101375798 A   3/2009
JP   09-061532 A   3/1997
(Continued)

OTHER PUBLICATIONS

Written Opinion dated Mar. 18, 2014 in PCT/JP2013/085131 filed Dec. 27, 2013 with English translation.
(Continued)

*Primary Examiner* — Allen C. Ho
(74) *Attorney, Agent, or Firm* — Oblon, McClelland, Maier & Neustadt, L.L.P.

(57) ABSTRACT

An X-ray CT apparatus includes: intensity distribution data acquiring circuitry is configured to acquire, by performing a first scan, intensity distribution data of X-rays being radiated from an X-ray tube and having passed through a subject; scan controlling circuitry is configured to estimate an X-ray dose with which it is possible to discriminate individual X-ray photons having passed through the subject based on the intensity distribution data and to cause a second scan that is for a photon counting CT purpose to be performed by causing the estimated dose of X-rays to be radiated from the X-ray tube to the subject; a counting result acquiring cir-
(Continued)

cuitry is configured to acquire, by the second scan, a counting result by counting the X-ray photons being radiated from the X-ray tube and having passed through the subject; and an image reconstructing circuitry is configured to reconstruct X-ray CT image data based on the counting result.

18 Claims, 8 Drawing Sheets

(52) U.S. Cl.
CPC .......... *A61B 6/4233* (2013.01); *A61B 6/4241* (2013.01); *A61B 6/4452* (2013.01); *A61B 6/488* (2013.01); *A61B 6/54* (2013.01); *A61B 6/542* (2013.01); *A61B 6/544* (2013.01); *A61B 6/545* (2013.01); *G06T 11/005* (2013.01); *A61B 6/032* (2013.01); *A61B 6/5205* (2013.01); *G06T 2211/408* (2013.01)

(58) Field of Classification Search
USPC .................. 378/16, 19, 98.8; 250/370.09
See application file for complete search history.

(56) References Cited

U.S. PATENT DOCUMENTS

| | | | | |
|---|---|---|---|---|
| 5,400,378 A * | 3/1995 | Toth | ............... | A61B 6/032 378/108 |
| 5,450,462 A * | 9/1995 | Toth | ............... | A61B 6/032 378/108 |
| 5,485,494 A * | 1/1996 | Williams | ............... | A61B 6/032 378/110 |
| 5,625,662 A * | 4/1997 | Toth | ............... | H05G 1/26 378/108 |
| 5,822,393 A * | 10/1998 | Popescu | ............... | A61B 6/032 378/108 |
| 5,867,555 A * | 2/1999 | Popescu | ............... | A61B 6/032 378/16 |
| 6,385,280 B1 * | 5/2002 | Bittl | ............... | A61B 6/032 378/106 |
| 6,404,844 B1 * | 6/2002 | Horiuchi | ............... | A61B 6/032 378/16 |
| 6,490,337 B1 * | 12/2002 | Nagaoka | ............... | A61B 6/032 378/16 |
| 6,507,639 B1 * | 1/2003 | Popescu | ............... | A61B 6/032 378/108 |
| 6,754,301 B2 * | 6/2004 | Horiuchi | ............... | A61B 6/032 378/16 |
| 6,904,127 B2 * | 6/2005 | Toth | ............... | A61B 6/032 378/108 |
| 6,987,828 B2 * | 1/2006 | Horiuchi | ............... | G01N 23/046 378/108 |
| 7,042,977 B2 * | 5/2006 | Dafni | ............... | A61B 6/032 378/16 |
| 7,082,183 B2 * | 7/2006 | Toth | ............... | A61B 6/032 378/16 |
| 7,103,139 B2 * | 9/2006 | Nagaoka | ............... | A61B 6/032 378/16 |
| 7,106,824 B2 * | 9/2006 | Kazama | ............... | A61B 6/032 378/110 |
| 7,142,630 B2 * | 11/2006 | Suzuki | ............... | A61B 6/542 378/108 |
| 7,203,270 B2 * | 4/2007 | Okumura | ............... | A61B 6/032 378/109 |
| 7,209,536 B2 * | 4/2007 | Walter | ............... | A61B 6/032 378/5 |
| 7,215,733 B2 * | 5/2007 | Nabatame | ............... | A61B 6/032 378/110 |
| 7,263,167 B2 * | 8/2007 | Walter | ............... | A61B 6/032 378/116 |
| 7,336,762 B2 * | 2/2008 | Seto | ............... | A61B 6/032 378/110 |
| 7,433,443 B1 * | 10/2008 | Tkaczyk | ............... | A61B 6/032 378/19 |
| 7,479,639 B1 * | 1/2009 | Shahar | ............... | G01T 1/17 250/370.06 |
| 7,613,274 B2 * | 11/2009 | Tkaczyk | ............... | A61B 6/032 378/19 |
| 7,636,416 B2 * | 12/2009 | Miyazaki | ............... | A61B 6/032 378/108 |
| 7,668,286 B2 * | 2/2010 | Tsuyuki | ............... | A61B 6/032 378/16 |
| 7,696,483 B2 * | 4/2010 | Tkaczyk | ............... | G01T 1/171 250/370.06 |
| 7,715,522 B2 * | 5/2010 | Goto | ............... | A61B 6/032 378/16 |
| 7,829,860 B2 * | 11/2010 | Nygard | ............... | G01T 1/2018 250/366 |
| 7,885,372 B2 * | 2/2011 | Edic | ............... | A61B 6/032 378/158 |
| 7,945,013 B2 * | 5/2011 | Goto | ............... | A61B 5/4869 378/16 |
| 8,111,803 B2 * | 2/2012 | Edic | ............... | A61B 6/4035 378/146 |
| 8,160,200 B2 * | 4/2012 | Tkaczyk | ............... | A61B 6/032 378/19 |
| 8,175,217 B2 * | 5/2012 | Sugaya | ............... | A61B 6/032 378/16 |
| 8,488,736 B2 * | 7/2013 | Hoffman | ............... | A61B 6/032 378/19 |
| 8,619,943 B2 * | 12/2013 | Flohr | ............... | A61B 6/032 378/19 |
| 8,744,039 B2 * | 6/2014 | Hirokawa | ............... | A61B 6/032 378/108 |
| 8,848,860 B2 * | 9/2014 | Yazaki | ............... | A61B 6/488 378/16 |
| 8,891,845 B2 * | 11/2014 | Ogawa | ............... | A61B 6/14 382/128 |
| 8,913,711 B2 * | 12/2014 | Moriyasu | ............... | A61B 6/03 378/4 |
| 8,988,267 B1 * | 3/2015 | Kimura | ............... | G01T 1/2928 341/155 |
| 9,044,189 B2 * | 6/2015 | Flohr | ............... | A61B 6/032 |
| 9,057,788 B2 * | 6/2015 | Abraham | ............... | G01T 1/1647 |
| 9,160,939 B2 * | 10/2015 | Funaki | ............... | H03M 1/145 |
| 9,164,183 B2 * | 10/2015 | Kraft | ............... | G01T 1/40 |
| 9,176,238 B2 * | 11/2015 | Herrmann | ............... | G01T 1/17 |
| 9,207,332 B2 * | 12/2015 | Spahn | ............... | G01T 1/17 |
| 9,268,035 B2 * | 2/2016 | Herrmann | ............... | G01T 1/17 |
| 9,285,326 B2 * | 3/2016 | Gagnon | ............... | A61B 6/032 |
| 9,301,378 B2 * | 3/2016 | Steadman Booker | .... | G01T 1/24 |
| 9,310,490 B2 * | 4/2016 | Abraham | ............... | G01T 1/17 |
| 9,335,424 B2 * | 5/2016 | Herrmann | ............... | G01T 1/171 |
| 9,354,331 B2 * | 5/2016 | Sagoh | ............... | A61B 6/032 |
| 9,417,339 B2 * | 8/2016 | Spahn | ............... | G01T 1/247 |
| 9,444,344 B2 * | 9/2016 | Kim | ............... | G01T 1/247 |
| 9,504,438 B2 * | 11/2016 | Proska | ............... | G01T 1/24 |
| 9,517,045 B2 * | 12/2016 | Kang | ............... | G01N 23/087 |
| 9,532,759 B2 * | 1/2017 | Taguchi | ............... | A61B 6/032 |
| 9,535,167 B2 * | 1/2017 | Proksa | ............... | G01T 1/171 |
| 9,535,172 B2 * | 1/2017 | Lee | ............... | G01T 1/24 |
| 9,538,107 B2 * | 1/2017 | Chappo | ............... | A61B 6/032 |
| 9,579,075 B2 * | 2/2017 | Besson | ............... | G01T 1/2985 |
| 9,595,101 B2 * | 3/2017 | Kato | ............... | G06T 7/0012 |
| 9,619,730 B2 * | 4/2017 | Pavlovich | ............... | A61B 6/5205 |
| 9,678,220 B2 * | 6/2017 | Herrmann | ............... | G01T 1/17 |
| 9,693,743 B2 * | 7/2017 | Arakita | ............... | G01T 1/1606 |
| 9,746,566 B2 * | 8/2017 | Herrmann | ............... | G01T 1/247 |
| 9,759,822 B2 * | 9/2017 | Daerr | ............... | G01T 1/17 |
| 2011/0243413 A1 | 10/2011 | Tkaczyk et al. | | |
| 2013/0010921 A1 | 1/2013 | Sagoh et al. | | |

FOREIGN PATENT DOCUMENTS

| | | |
|---|---|---|
| JP | 2008-018044 A | 1/2008 |
| JP | 2011-206536 A | 10/2011 |
| JP | 2012-034901 A | 2/2012 |

(56) References Cited

FOREIGN PATENT DOCUMENTS

JP 2012-187143 A 10/2012
WO WO 2012/173206 A1 12/2012

OTHER PUBLICATIONS

Combined Office Action and Search Report dated Jan. 25, 2017 in Chinese Patent Application No. 201380061376.7 (with English Translation of Categories of Cited Documents).
English Translation of the International Search Report dated Mar. 18, 2014 in PCT/JP2013/085131 filed Dec. 27, 2013.

\* cited by examiner

| BULB PHASE | INTENSITY DISTRIBUTION DATA | X-RAY DOSE |
|---|---|---|
| α1 | I1 | D1 |
| α2 | I2 | D2 |
| ⋮ | ⋮ | ⋮ |

US 9,924,916 B2

X-RAY CT APPARATUS AND CONTROLLING METHOD

CROSS-REFERENCE TO RELATED APPLICATIONS

This application is a continuation of PCT international application Ser. No. PCT/JP2013/085131 filed on Dec. 27, 2013 which designates the United States, incorporated herein by reference, and which claims the benefit of priority from Japanese Patent Application No. 2012-285234, filed on Dec. 27, 2012, the entire contents of which are incorporated herein by reference.

FIELD

Embodiments described herein relate generally to an X-ray CT apparatus and a controlling method.

BACKGROUND

In recent years, X-ray CT apparatuses that perform a photon counting Computed Tomography (CT) by employing a photon-counting type detector have been developed. Unlike integral-type detectors used in conventional X-ray CT apparatuses, the photon-counting type detector outputs signals that make it possible to individually count photons derived from X-rays that have passed through an examined subject (hereinafter, a "subject"). Accordingly, by performing the photon counting CT, it is possible to reconstruct an X-ray CT image having a high Signal-per-Noise (S/N) ratio.

Further, the signals output by the photon-counting type detector can be used for measuring (discriminating) an energy level of each of the counted photons. Accordingly, by performing the photon counting CT, it is possible to image data acquired by radiating X-rays while using one type of X-ray tube voltage in such a manner that the data is divided into a plurality of energy components. For example, by performing the photon counting CT, it is possible to generate an image that makes it possible to identify one or more substances by utilizing differences in K absorption edges.

By performing the photon counting CT, it is possible to accurately measure the radiation (the X-rays) if the dose of the incident radiation is small. However, during the photon counting CT, if the dose of the incident radiation is large, a phenomenon called "pile-up" may occur where pieces of data obtained by counting the individual photons pile up. In that situation, because it is not possible to separate the individual photons from one another, miscounts occur where the count characteristics are not linear.

DETAILED DESCRIPTION

Figure 1A:
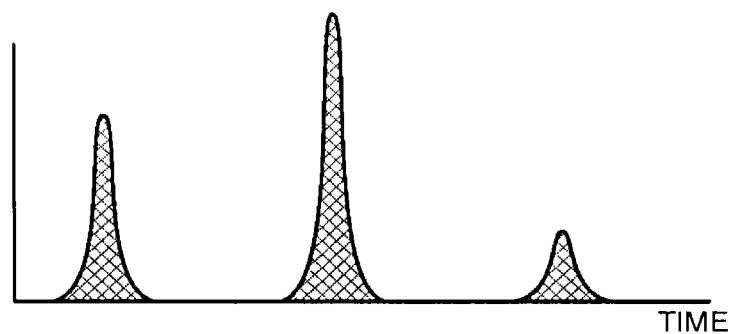
FIG. 1A, FIG. 1B and FIG. 1C are drawings for explaining a pile-up phenomenon.

An X-ray CT apparatus includes: intensity distribution data acquiring circuitry is configured to acquire, by performing a first scan, intensity distribution data of X-rays being radiated from an X-ray tube and having passed through a subject; scan controlling circuitry is configured to estimate an X-ray dose with which it is possible to discriminate individual X-ray photons having passed through the subject based on the intensity distribution data and to cause a second scan that is for a photon counting CT purpose to be performed by causing the estimated dose of X-rays to be radiated from the X-ray tube to the subject; a counting result acquiring circuitry is configured to acquire, by the second scan, a counting result by counting the X-ray photons being radiated from the X-ray tube and having passed through the subject; and an image reconstructing circuitry is configured to reconstruct X-ray CT image data based on the counting result.

An X-ray CT apparatus according to an embodiment includes an intensity distribution data acquiring unit, a scan controlling unit, a counting result acquiring unit, and an image reconstructing unit. The intensity distribution data acquiring unit acquires, by performing a first scan, intensity distribution data of X-rays that are radiated from an X-ray tube and that have passed through a subject. The scan controlling unit estimates an X-ray dose with which it is possible to discriminate individual X-ray photons that have passed through the subject based on the intensity distribution data and causes a second scan that is for a photon counting CT purpose to be performed by causing the estimated dose of X-rays to be radiated from the X-ray tube to the subject. The counting result acquiring unit acquires, by the second scan, a counting result by counting the X-ray photons that are radiated from the X-ray tube and that have passed through the subject. The image reconstructing unit reconstructs X-ray CT image data based on the counting result.

Exemplary embodiments of an X-ray Computed Tomography (CT) apparatus will be explained in detail below, with reference to the accompanying drawings.

The X-ray CT apparatuses explained in the exemplary embodiments below are capable of performing a photon counting CT. In other words, the X-ray CT apparatuses explained in the exemplary embodiments below are capable of reconstructing X-ray CT image data having a high S/N ratio, by counting X-rays that have passed through a subject by employing a photon-counting type detector, instead of a conventional integral-type detector (that uses a current mode measuring method).

First Embodiment

Before explaining an X-ray CT apparatus according to a first embodiment, the photon counting CT will be explained.

During the photon counting CT, the amount of light (X-rays) is measured by counting the number of photons. The larger the number of photons per unit time is, the stronger the light (the X-rays) is. Further, although each photon has a different level of energy, the photon counting CT makes it possible to obtain information about energy components of the X-rays by measuring the energy of the photons. In other words, by performing the photon counting CT, it is possible to image data acquired by radiating X-rays while using one type of X-ray tube voltage in such a manner that the data is divided into a plurality of energy components. For example, by performing the photon counting CT, it is possible to obtain image data that makes it possible to identify substances by utilizing differences in K absorption edges.

During the photon counting CT, however, if the dose of the incident radiation is large, a phenomenon called "pile-up" may occur where pieces of data obtained by counting the individual photons pile up. When the pile-up has occurred, because it is not possible to separate the individual photons from one another, "miscounts" occur where the count characteristics are not linear.

Figure 1B:
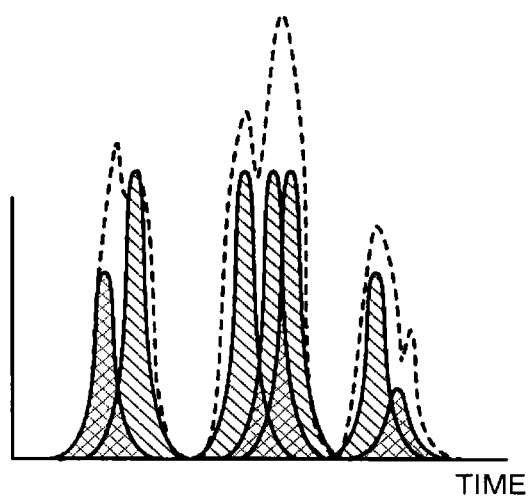
Figure 10:
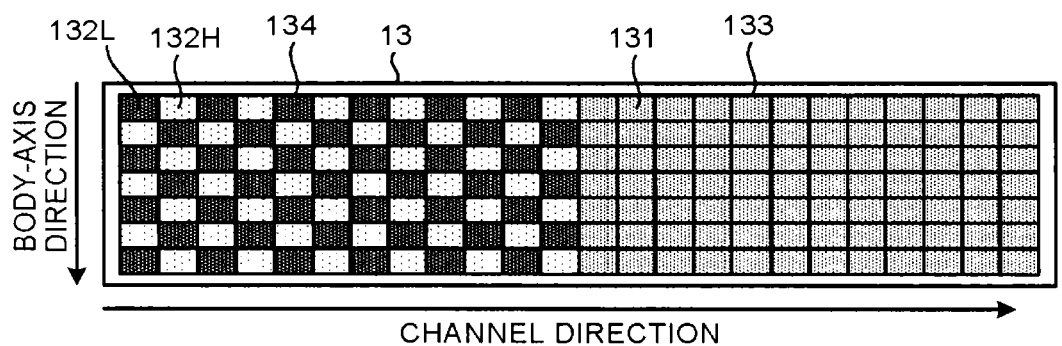
FIG. 10 and FIG. 11 are drawings for explaining modified examples.

FIGS. 1A, 1B, and 10 are drawings for explaining the pile-up. Sensors (elements) employed in a photon-counting type detector output an electric signal of one pulse when a photon has become incident thereto. If the light is weak, because the incident intervals of the photons are longer as illustrated in FIG. 1A, it is possible to discriminate the pulses that are output from the sensors.

On the contrary, if the light is strong and the incident intervals of the photons are shorter, the pulses that are output from the sensors pile up as illustrated in FIG. 1B, and it is therefore not possible to discriminate the individual pulses. Specifically, a plurality of pulses piling up are seemingly discriminated as a single pulse (see the waveform drawn with a dotted line in FIG. 1B). As a result, miscounts occur where the linearity between the number of photons that have actually become incident to the sensors and the counted value of the pulses (the number of pulses) output by the sensors is lost. In other words, as illustrated in FIG. 10, the higher the intensity of the X-rays is, the less the count for the number of pulses has been, as compared to the actual number of photons.

Figure 2:
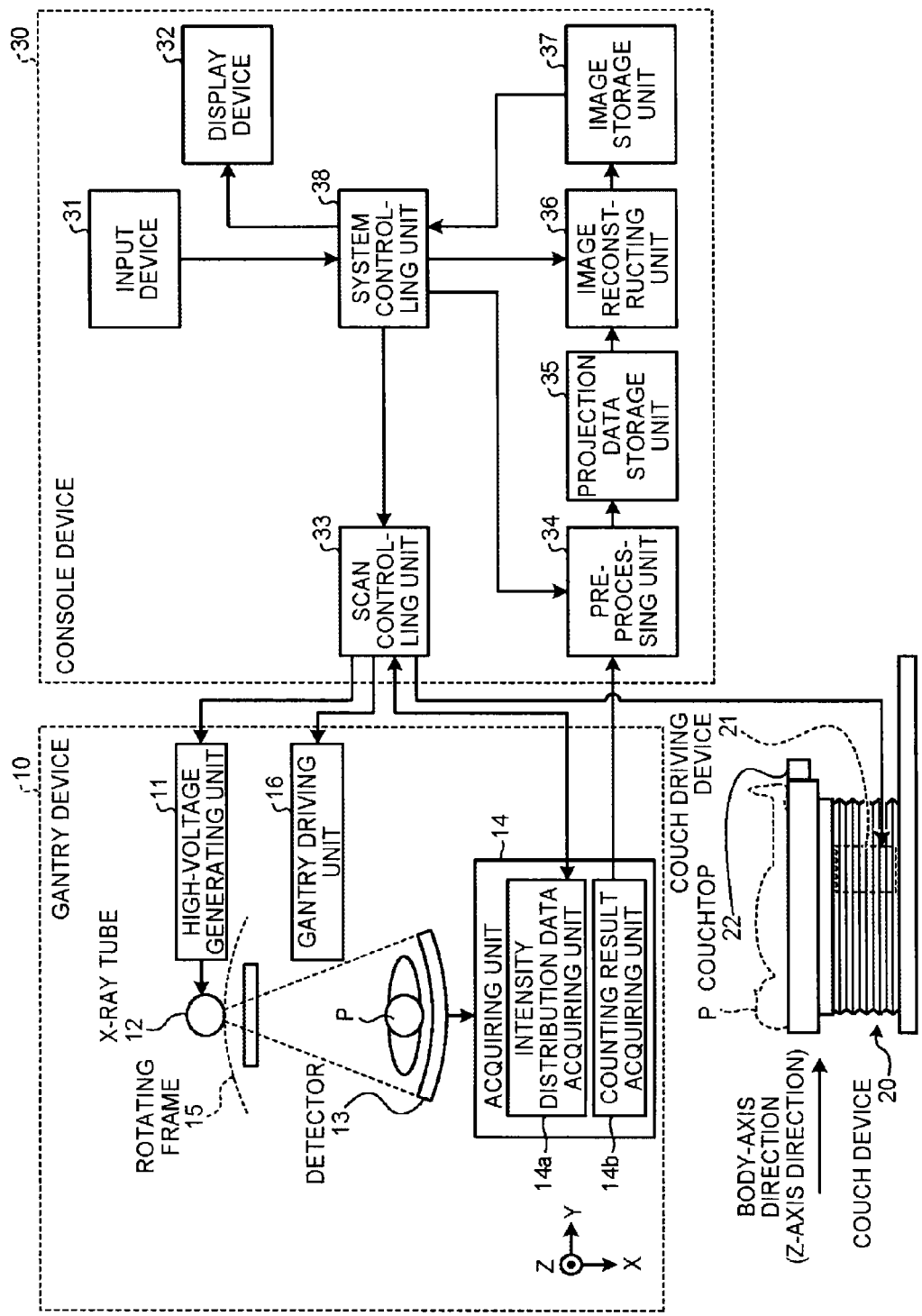
FIG. 2 is a drawing of an exemplary configuration of an X-ray CT apparatus according to a first embodiment.

To cope with this situation, the X-ray CT apparatus according to the first embodiment is configured as described below, for the purpose of reducing the occurrence of miscounts. FIG. 2 is a drawing of an exemplary configuration of the X-ray CT apparatus according to the first embodiment. As illustrated in FIG. 2, the X-ray CT apparatus according to the first embodiment includes a gantry device 10, a couch device 20, and a console device 30.

The gantry device 10 is a device that radiates X-rays to a subject P and acquires data related to X-rays that have passed through the subject P. The gantry device 10 includes a high-voltage generating unit 11, an X-ray tube 12, a detector 13, an acquiring unit 14, a rotating frame 15, and a gantry driving unit 16.

The rotating frame 15 is an annular frame that supports the X-ray tube 12 and the detector 13 so as to face each other while the subject P is interposed therebetween and that is rotated by the gantry driving unit 16 (explained later) at a high speed on a circular trajectory centered on the subject P.

The X-ray tube 12 is a vacuum tube that radiates the X-ray beams to the subject P by using a high voltage supplied by the high-voltage generating unit 11 (explained later). In conjunction with rotations of the rotating frame 15, the X-ray tube 12 radiates the X-ray beams to the subject P.

The high-voltage generating unit 11 is a device that supplies the high voltage to the X-ray tube 12. The X-ray tube 12 generates the X-rays by using the high voltage supplied from the high-voltage generating unit 11. In other words, the high-voltage generating unit 11 adjusts the dose of the X-rays radiated to the subject P, by adjusting an X-ray tube voltage and an X-ray tube current supplied to the X-ray tube 12.

By driving the rotating frame 15 to rotate, the gantry driving unit 16 causes the X-ray tube 12 and the detector 13 to turn on the circular trajectory centered on the subject P.

The detector 13 includes a first element group that detects an intensity of X-rays that have passed through the subject P and a second element group that counts light beams (X-ray photons) derived from the X-rays that have passed through the subject P. The first element group is structured by using a plurality of first elements that detect the intensity of the X-rays. The plurality of first elements may be configured with photodiodes, for example. The second element group is structured by using a plurality of second elements served as photon counting sensors. The plurality of second elements may be configured with cadmium-telluride(CdTe)-based semiconductors, for example. In other words, the plurality of second elements are direct-conversion-type semiconductors that directly convert the incident X-rays to electric signals. The first embodiment is also applicable to a situation where the plurality of second elements are indirect-conversion-type, which are each configured with a scintillator and a photomultiplier tube.

Figure 3:
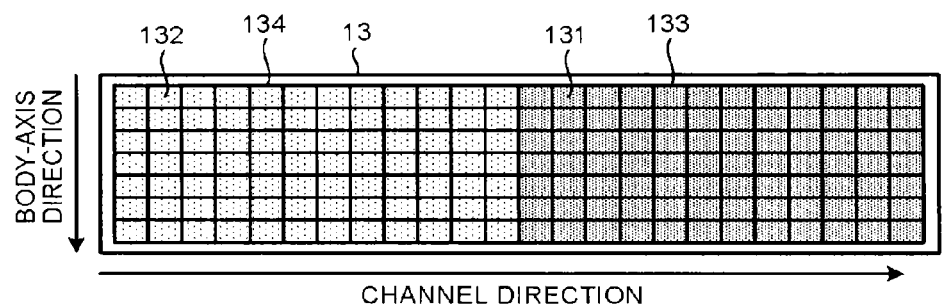
FIG. 3 is a drawing for explaining an example of a detector according to the first embodiment.

Further, the detector 13 according to the first embodiment is divided into a first area 133 and a second area 134 along the channel direction. Further, the first element group is arranged in the first area, whereas the second element group is arranged in the second area. FIG. 3 is a drawing for explaining an example of the detector 13 according to the first embodiment.

As illustrated in FIG. 3, in the detector 13 according to the first embodiment, a plurality of rows in each of which elements are arranged in the channel direction (the Y-axis direction in FIG. 2) are arranged along the body-axis direction of the subject P (the Z-axis direction in FIG. 2). Further, as illustrated in FIG. 3, the detector 13 according to the first embodiment is divided into a first area 133 and a second area 134 along the channel direction. In the first area 133, the plurality of first elements 131 configured with photodiodes are arranged two-dimensionally. In the second area 134, the plurality of second elements 132 served as photon counting sensors are arranged two-dimensionally. The first area 133 and the second area 134 are substantially equal in size.

By employing the plurality of first elements 131 arranged two-dimensionally, the detector 13 according to the first embodiment detects the intensity of the X-rays that are radiated from the X-ray tube 12 and that have passed through the subject P. Further, by employing the plurality of second elements 132 arranged two-dimensionally, the detector 13 according to the first embodiment outputs electric signals. By using the electric signals, it is possible to count the X-ray photons that are radiated from the X-ray tube 12 and that have passed through the subject P and to measure energy levels of the counted X-ray photons.

Returning to the description of FIG. 2, the acquiring unit 14 acquires various types of information from the output signals of the detector 13. As illustrated in FIG. 2, the acquiring unit 14 according to the first embodiment includes an intensity distribution data acquiring unit 14a and a counting result acquiring unit 14b. The intensity distribution data acquiring unit 14a acquires intensity distribution data of the X-rays that are radiated from the X-ray tube 12 and that have passed through the subject P. Specifically, the intensity distribution data acquiring unit 14a acquires the intensity distribution data for each of phases of the X-ray tube 12 (X-ray tube phases).

Further, the counting result acquiring unit 14b acquires a counting result by counting the X-ray photons that are radiated from the X-ray tube 12 and that have passed through the subject P. Specifically, the counting result acquiring unit 14b acquires, for each of the phases of the X-ray tube 12 (the X-ray tube phases), incident positions (detection positions) of the X-ray photons counted by discriminating the pulses output by the plurality of second elements 132 and an energy value of the X-ray photons, as the counting result. For example, the counting result acquiring unit 14b uses the positions of the plurality of second elements 132 that output the pulses used in the counting process as the incident positions. Further, for example, the counting result acquiring unit 14b calculates the energy value from a peak value of the pulses and a response function unique to the X-ray CT apparatus. Alternatively, for example, the counting result acquiring unit 14b may calculate the energy value by integrating the intensities of the pulses.

For example, the counting result may be information indicating that "in an X-ray tube phase "α1", the counted value of photons having an energy level "E1" is "N1", whereas the counted value of photons having an energy value "E2" is "N2", at a second element 132 in an incident position "P11"". Alternatively, for example, the counting result may be information indicating that "in a X-ray tube phase "α1", the counted value per unit time of photons having an energy level "E1" is "n1", whereas the counted value per unit time of photons having an energy level "E2" is "n2", at a second element 132 in an incident position "P11"". Alternatively, for example, the energy level "E1" may be expressed as an energy range "E1 to E2". In that situation, for example, the counting result may be information indicating that "in an X-ray tube phase "α1", the counted value of photons having an energy range "E1 to E2" is "NN1", at a second element 132 in an incident position "P11". The energy range is served as an energy discrimination region used by the counting result acquiring unit 14b to discriminate and allocate the energy value to regions having a coarse granularity level.

The intensity distribution data acquiring unit 14a transmits the acquired intensity distribution data to a scan controlling unit 33 (explained later) included in the console device 30. Further, the counting result acquiring unit 14b transmits the acquired counting result to a preprocessing unit 34 (explained later) included in the console device 30.

In this situation, the intensity distribution data is acquired by performing a first scan, which is for the purpose of acquiring the intensity distribution data. Further, after an X-ray dose adjustment is made on the basis of the intensity distribution data, the counting result is acquired by performing a second scan, which is for the purpose of acquiring the counting result. A method for performing the first and the second scans and the X-ray dose adjustment based on the intensity distribution data will be explained in detail later.

The couch device 20 is a device on which the subject P is placed and includes a couchtop 22 and a couch driving device 21. The couchtop 22 is a plate on which the subject P is placed. The couch driving device 21 moves the couchtop 22 in the Z-axis direction so as to move the subject P into the rotating frame 15.

For example, the gantry device 10 performs a helical scan, which is to helically scan the subject P by causing the rotating frame 15 to rotate while moving the couchtop 22. In another example, the gantry device 10 performs a conventional scan, which is to scan the subject P on the circular trajectory by causing the rotating frame 15 to rotate while the subject P is fixed in a position after the couchtop 22 has been moved.

The console device 30 receives an operation performed on the X-ray CT apparatus by an operator and reconstructs X-ray CT image data by using the count information acquired by the gantry device 10. As illustrated in FIG. 2, the console device 30 includes an input device 31, a display device 32, the scan controlling unit 33, the preprocessing unit 34, a projection data storage unit 35, an image reconstructing unit 36, an image storage unit 37, and a system controlling unit 38.

The input device 31 includes a mouse, a keyboard, and the like used by the operator of the X-ray CT apparatus to input various types of instructions and various types of settings. The input device 31 transfers information about the instructions and the settings received from the operator to the system controlling unit 38. For example, the input device 31 receives, from the operator, a reconstructing condition used for reconstructing the X-ray CT image data, an image processing condition for the X-ray CT image data, and the like.

The display device 32 is a monitor referred by the operator. Under control of the system controlling unit 38, the display device 32 displays the X-ray CT image data for the operator and displays a Graphical User Interface (GUI) used for receiving the various types of instructions and the various types of settings from the operator via the input device 31.

Under the control of the system controlling unit 38 (explained later), the scan controlling unit 33 controls count information acquiring processes performed by the gantry device 10, by controlling the operations of the high-voltage generating unit 11, the gantry driving unit 16, the acquiring unit 14, and the couch driving device 21.

Specifically, the scan controlling unit 33 according to the first embodiment causes the gantry device 10 to perform the first scan and further receives the intensity distribution data from the intensity distribution data acquiring unit 14a. Further, the scan controlling unit 33 according to the first embodiment determines a scan condition on the basis of the intensity distribution data and causes the gantry device 10 to perform the second scan. The scan controlling unit 33 according to the first embodiment causes the first scan to be performed by employing the first element group (the plurality of first elements 131). Also, the scan controlling unit 33 according to the first embodiment causes the second scan to be performed by employing the second element group (the plurality of second elements 132). Controlling processes performed by the scan controlling unit 33 according to the first embodiment will be explained in detail later.

The preprocessing unit 34 generates projection data by performing a correcting process such as a logarithmic transformation process, an offset correction, a sensitivity correction, a beam hardening correction, and/or the like, on the counting result transmitted from the counting result acquiring unit 14b.

The projection data storage unit 35 stores the projection data generated by the preprocessing unit 34 In other words, the projection data storage unit 35 stores the projection data used for reconstructing the X-ray CT image data.

The image reconstructing unit 36 reconstructs the X-ray CT image data by, for example, performing a back-projection process on the projection data stored in the projection data storage unit 35. Examples of the back-projection process include one that uses a Filtered Back Projection (FBP) method. Alternatively, the image reconstructing unit 36 may perform the reconstructing process by implementing a successive approximation method, for example. Further, the image reconstructing unit 36 generates image data by performing various types of image processing processes on the X-ray CT image data. The image reconstructing unit 36 stores the reconstructed X-ray CT image data and the image data generated by performing the various types of image processing processes, in the image storage unit 37.

In this situation, the projection data generated from the counting result obtained from the photon counting CT contains information about the energy of the X-rays attenuated by passing through the subject P. For this reason, the image reconstructing unit 36 is able to, for example, reconstruct X-ray CT image data representing a specific energy component. Further, the image reconstructing unit 36 is able to, for example, reconstruct X-ray CT image data representing each of a plurality of energy components.

Further, for example, the image reconstructing unit 36 is able to generate image data in which a tone corresponding to an energy component is assigned to each of the pixels in the X-ray CT image data representing the plurality of energy components, so that a plurality of pieces of X-ray CT image data that are color-coded corresponding to the plurality of energy components are superimposed. Further, the image reconstructing unit 36 is able to generate image data that makes it possible to identify substances by utilizing the K absorption edge unique to each substance. Other examples of image data generated by the image reconstructing unit 36 include monochrome X-ray image data, density image data, and effective atomic number image data.

The system controlling unit 38 exercises overall control of the X-ray CT apparatus, by controlling the operations of the gantry device 10, the couch device 20, and the console device 30. Specifically, the system controlling unit 38 controls a CT scan performed by the gantry device 10, by controlling the scan controlling unit 33. Further, the system controlling unit 38 controls the image reconstructing process and the image generating process performed by the console device 30, by controlling the preprocessing unit 34 and the image reconstructing unit 36. Further, the system controlling unit 38 exercises control so that the various types of image data stored in the image storage unit 37 are displayed on the display device 32.

An overall configuration of the X-ray CT apparatus according to the first embodiment has thus been explained. The X-ray CT apparatus according to the first embodiment configured as described above reduces the occurrence of miscounts, by using the controlling processes explained below performed by the scan controlling unit 33.

First, the intensity distribution data acquiring unit 14a acquires, by performing the first scan, the intensity distribution data of the X-rays that are radiated from the X-ray tube 12 and that have passed through the subject P. As explained above, in the detector 13 according to the first embodiment, the first element group (the plurality of first elements 131) is two-dimensionally arranged in the first area 133, whereas the second element group (the plurality of second elements 132) is two-dimensionally arranged in the second area 134. Thus, when performing the first scan, the scan controlling unit 33 according to the first embodiment moves the first area 133 in which the plurality of first elements 131 are two-dimensionally arranged, to a position facing the X-ray tube 12. In other words, when performing the first scan, the scan controlling unit 33 moves the first area 133 to an X-ray radiation area of the X-ray tube 12.

Figure 4:
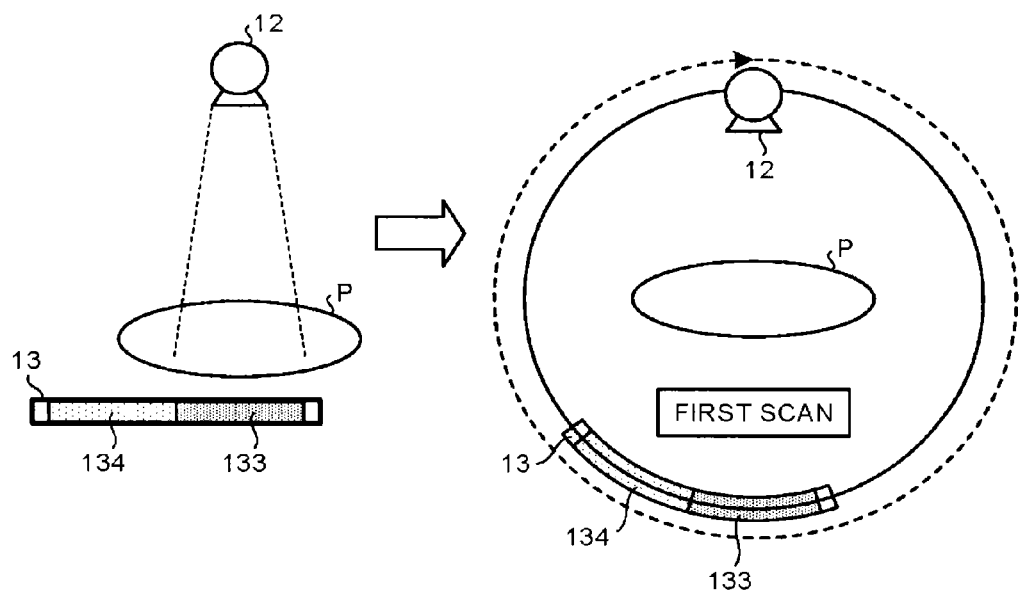
FIG. 4 is a drawing for explaining a first scan according to the first embodiment.

To achieve this control, in one example according to the first embodiment, a moving mechanism (not shown) used for moving the detector 13 in a circumferential direction is installed on the inside of the rotating frame 15. FIG. 4 is a drawing for explaining the first scan according to the first embodiment. For example, according to an instruction from the scan controlling unit 33, the gantry driving unit 16 moves the detector 13 until the first area 133 comes to the position facing the X-ray tube 12, by driving the moving mechanism. In other words, as illustrated in FIG. 4, the detector 13 is moved until the first area 133 comes to the position facing the X-ray tube 12, along the circumferential direction of the rotating frame 15.

Further, as illustrated in FIG. 4, the scan controlling unit 33 causes the first scan to be performed with performing X-ray radiation all around the subject P. In other words, the first scan is performed while the first area 133 is being maintained in the position facing the X-ray tube 12. The first scan performed for the purpose of measuring the intensity distribution data is called an Intensity Scan (IS). For example, the X-ray dose (D0) radiated from the X-ray tube 12 in the first scan may be an X-ray dose compliant with an image taking condition that is set by the operator or may be an X-ray dose that is initially set for the first scan purpose.

Figures 5, 6:
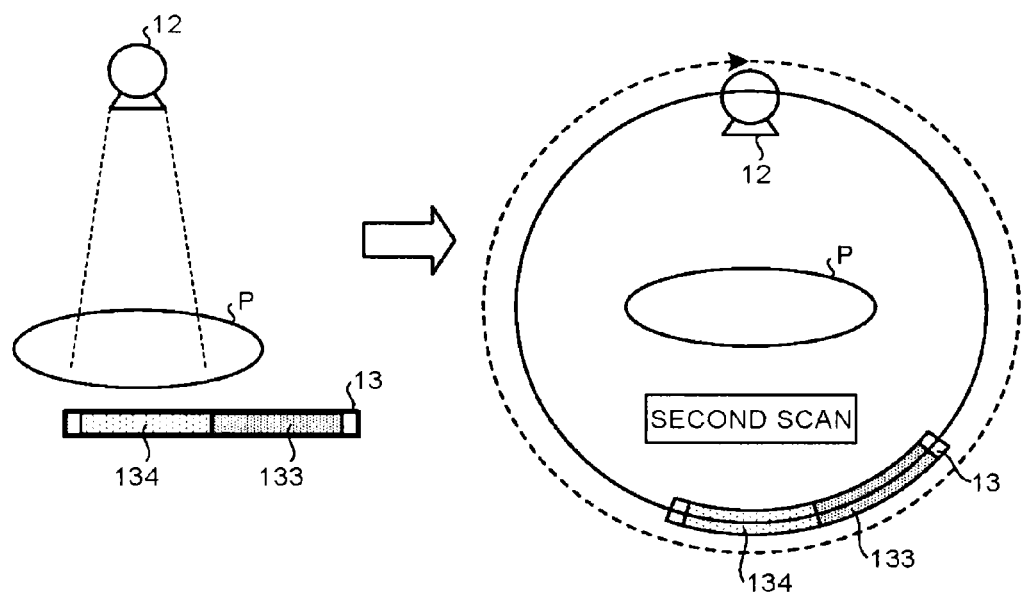
FIG. 5 is a drawing for explaining a scan controlling unit according to the first embodiment.
FIG. 6 is a drawing for explaining a second scan according to the first embodiment.

As a result, the intensity distribution data acquiring unit 14a acquires the intensity distribution data corresponding to all around the subject P. After that, on the basis of the intensity distribution data, the scan controlling unit 33 estimates an X-ray dose with which it is possible to discriminate the individual X-ray photons that have passed through the subject P. Specifically, on the basis of the intensity distribution data corresponding to all around the subject P acquired in the first scan, the scan controlling unit 33 estimates the X-ray dose for each of the X-ray tube phases in which a counting result is to be acquired. FIG. 5 is a drawing for explaining the scan controlling unit according to the first embodiment.

For example, as illustrated in FIG. 5, on the basis of "intensity distribution data: I1" in the "X-ray tube phase: α1", the scan controlling unit 33 estimates that an X-ray dose to be radiated from the X-ray tube 12 in the "X-ray tube phase: α1" during the second scan will be "D1". For example, the scan controlling unit 33 specifies a maximum X-ray intensity "I1(max)" from the "intensity distribution data: I1". After that, the scan controlling unit 33 compares "I1(max)" with a threshold value "Ith". For example, "Ith" is an upper-limit threshold value that is set in advance on the basis of physical properties of the plurality of first elements 131 and the plurality of second elements 132. The threshold value "Ith" denotes an X-ray intensity observed when X-rays corresponding to the maximum X-ray dose with which the plurality of second elements 132 are able to avoid the occurrence of a pile-up become incident to the plurality of first elements 131 while the subject P is not placed. For example, the threshold value "Ith" is a value obtained by calibrating the X-ray CT apparatus before an image taking process, or at the time of a periodic inspection, or at the time of factory shipment.

If "I1(max)" is larger than "Ith", the scan controlling unit 33 estimates that, for example, "D1=D0×(I1(max)/Ith)" will be satisfied. On the contrary, if "I1(max)" is equal to or smaller than "Ith", the scan controlling unit 33 estimates that, for example, "D1=D0" will be satisfied. As a result, the scan controlling unit 33 has estimated the X-ray dose "D1" with which it is possible to discriminate the individual X-ray photons that have passed through the subject P, by using the output pulses from the second element group in the "X-ray tube phase: α1" in which a counting result is to be acquired in the second scan. By performing a similar process, the scan controlling unit 33 estimates, as illustrated in FIG. 5, that an X-ray dose radiated from the X-ray tube 12 in a "X-ray tube phase: α2" during the second scan will be "D2", on the basis of "intensity distribution data: I2" in the "X-ray tube phase: α2". By performing the processes described above, the scan controlling unit 33 estimates an X-ray dose (an optimal X-ray dose) for each of all the X-ray tube phases required under the image taking condition that was set for performing the photon counting CT.

The X-ray doses radiated from the X-ray tube 12 in the mutually-different X-ray tube phases are not necessarily constant. For this reason, when a full reconstruction is performed so as to reconstruct tomography images from projection data (counting results) in a "360-degree range", it is desirable to acquire the intensity distribution data corresponding to all around the subject P. However, for example, the scan controlling unit 33 may estimate the minimum value among the optimal X-ray doses estimated for the mutually-different X-ray tube phases, as an optimal X-ray dose for all the X-ray tube phases. In contrast, when a half reconstruction is performed so as to reconstruct tomography images from projection data (counting results) in a "(180+α) degree range where α is a fan angle", it is also acceptable to acquire intensity distribution data corresponding to "(180+α) degrees".

After that, the scan controlling unit 33 causes a second scan that is for a photon counting CT purpose to be performed, by causing the estimated dose of X-rays to be radiated from the X-ray tube 12 to the subject P. When performing the second scan, the scan controlling unit 33 according to the first embodiment moves the second area 134 in which the plurality of second elements 132 are two-dimensionally arranged, to the position facing the X-ray tube 12. In other words, when performing the second scan, the scan controlling unit 33 moves the second area 134 to the X-ray radiation area of the X-ray tube 12. FIG. 6 is a drawing for explaining the second scan according to the first embodiment. For example, according to an instruction from the scan controlling unit 33, the gantry driving unit 16 moves the detector 13 until the second area 134 comes to the position facing the X-ray tube 12, by driving the moving mechanism described above, as illustrated in FIG. 6. In other words, as illustrated in FIG. 6, the detector 13 is moved until the second area 134 comes to the position facing the X-ray tube 12, along the circumferential direction of the rotating frame 15.

After that, the scan controlling unit 33 notifies the high-voltage generating unit 11 of control values (e.g., an X-ray tube voltage and an X-ray tube current) by which the optimal X-ray dose is achieved in each of the X-ray tube phases. Accordingly, the high-voltage generating unit 11 supplies the X-ray tube voltage and the X-ray tube current by which the optimal X-ray dose is achieved in each of the X-ray tube phases, to the X-ray tube 12. Thus, as illustrated in FIG. 6, the scan controlling unit 33 causes the second scan to be performed with X-ray radiation all around the subject P. In other words, the second scan is performed while the second area 134 is being maintained in the position facing the X-ray tube 12. FIG. 6 illustrates the second scan that is performed when a full reconstruction is performed. The second scan for the photon counting CT purpose is called a Photon Counting Scan (PCS).

As explained above, the scan controlling unit 33 causes the first scan and the second scan, once each, to be performed alternately and successively on the same trajectory. For example, to reconstruct X-ray CT image data on one axial cross-section by performing a conventional scan, the scan controlling unit 33 causes the first scan to be performed, and subsequently causes the second scan to be performed on the same trajectory as that of the first scan.

Because the detector 13 is an area detector, the X-ray CT apparatus is able to reconstruct a plurality of axial cross-sections by performing a conventional scan. For this reason, by implementing a step-and-shoot method by which a conventional scan is performed while moving the couchtop 22 to positions arranged at regular intervals, the X-ray CT apparatus is able to reconstruct three-dimensional X-ray CT image data of the subject P. When implementing the step-and-shoot method also, every time the position of the couchtop 22 is moved, the scan controlling unit 33 causes the first scan to be performed, and subsequently causes the second scan to be performed on the same trajectory as that of the first scan.

Further, in recent years, a "helical shuttle scan" is also in use, by which the couchtop 22 is continuously reciprocated while the X-ray tube 12 is continuously rotated on a circular trajectory centered on the subject P. During the "helical shuttle scan", if it is possible to exercise control in such an manner that a going scan and a coming scan are on the same trajectory, it is possible to apply the controlling process described above to a helical scan, by arranging the going scan to be the first scan and arranging the coming scan to be the second scan.

Figure 7:
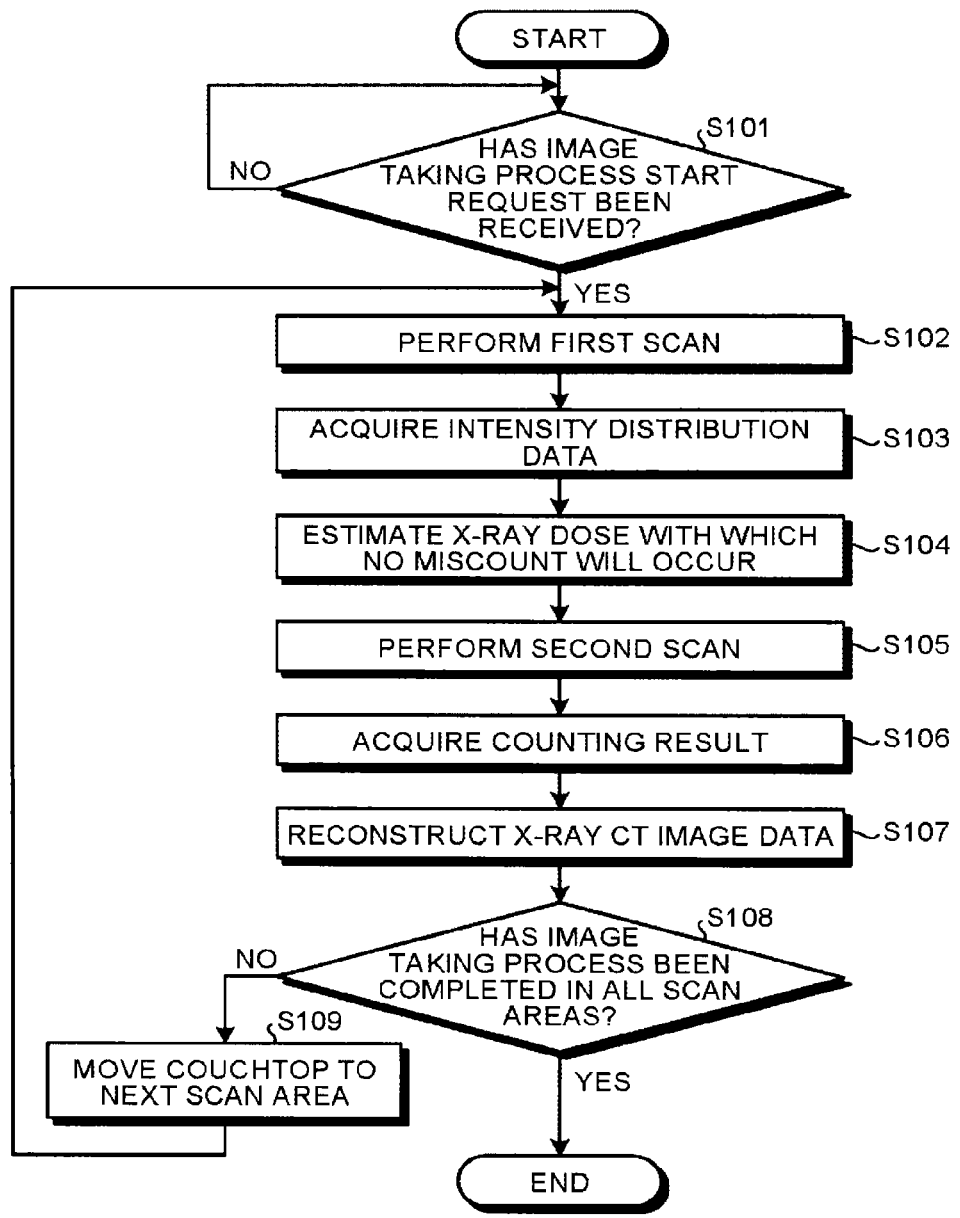
FIG. 7 is a flowchart for explaining an example of a process performed by the X-ray CT apparatus according to the first embodiment.

Next, a process performed by the X-ray CT apparatus according to the first embodiment will be explained, with reference to FIG. 7. FIG. 7 is a flowchart for explaining an example of the process performed by the X-ray CT apparatus according to the first embodiment. The flowchart in FIG. 7 illustrates an exemplary process performed when the step-and-shoot method is implemented.

As illustrated in FIG. 7, the system controlling unit 38 included in the X-ray CT apparatus according to the first embodiment judges whether an image taking process start request has been received from the operator (step S101). If no image taking process start request has been received (step S101: No), the system controlling unit 38 stands by until an image taking process start request is received.

On the contrary, if an image taking process start request has been received (step S101: Yes), the scan controlling unit 33 causes the first scan to be performed by controlling the gantry driving unit 16, the high-voltage generating unit 11, and the like (step S102). After that, the intensity distribution data acquiring unit 14a acquires intensity distribution data (step S103). Subsequently, the system controlling unit 38 estimates an X-ray dose with which no miscount will occur, on the basis of the intensity distribution data (step S104) and causes the second scan to be performed (step S105).

After that, the counting result acquiring unit 14b acquires a counting result (step S106), and the image reconstructing unit 36 reconstructs X-ray CT image data (step S107). Subsequently, the scan controlling unit 33 judges whether the image taking process has been completed in all the scan areas (step S108). If the image taking process has not been completed in all the scan areas (step S108: No), the scan controlling unit 33 moves the couchtop 22 to the next scan area by controlling the couch driving device 21 (step S109), so that the process returns to step S102 where the scan controlling unit 33 causes the first scan to be performed in the next scan area.

On the contrary, the image taking process has been completed in all the scan areas (step S108: Yes), the scan controlling unit 33 ends the process.

As explained above, in the first embodiment, the X-ray intensity is measured in advance by performing the first scan (IS) so as to estimate the X-ray dose with which it is possible to discriminate the individual X-ray photons, before performing the second scan (PCS). As a result, according to the first embodiment, it is possible to lower the possibility of being unable to discriminate the individual photons due to excessive X-rays becoming incident. Consequently, according to the first embodiment, it is possible to reduce the occurrence of miscounts. Further, according to the first embodiment, because the X-ray dose is optimized, it is possible to avoid unnecessary exposure to the X-ray radiation during the second scan.

Further, for the purpose of preventing an increase in the processing load of the console device 30, the scan controlling unit 33 may suspend the data output from the counting result acquiring unit 14b when performing the first scan and may suspend the data output from the intensity distribution data acquiring unit 14a when performing the second scan. Further, for the purpose of preventing an increase in the processing load of the acquiring unit 14, the scan controlling unit 33 may block the output path from the second element group to the acquiring unit 14 when performing the first scan and may block the output path and suspend the output from the first element group to the acquiring unit 14 when performing the second scan. In one example, the scan controlling unit 33 may stop the operation of a circuit that reads the output signals from the second element group when performing the first scan and may stop the operation of a circuit that reads the output signals from the first element group when performing the second scan.

Further, in the description above, the example is explained in which the position of the detector 13 is moved along the circumferential direction, to change the relative positional relationship of the X-ray tube 12 and the detector 13, between when performing the first scan and when performing the second scan. However, the first embodiment may be configured so that, the position of the X-ray tube 12 is moved along the circumferential direction, to change the relative positional relationship of the X-ray tube 12 and the detector 13, between when performing the first scan and when performing the second scan.

Second Embodiment

In a second embodiment, an example in which the detector 13 is configured differently from the first embodiment will be explained. Except for the different configuration of the detector 13, an X-ray CT apparatus according to the second embodiment is the same as the X-ray CT apparatus according to the first embodiment explained with reference to FIG. 1.

Figure 8A:
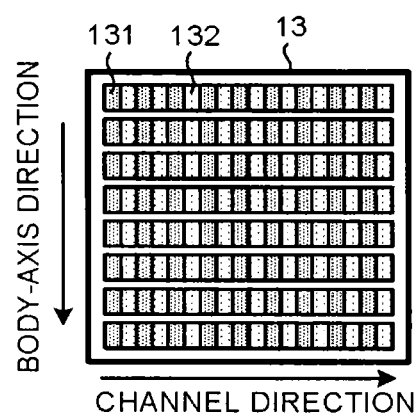
FIG. 8A and FIG. 8B are drawings for explaining an example of a detector according to a second embodiment.
Figure 8B:
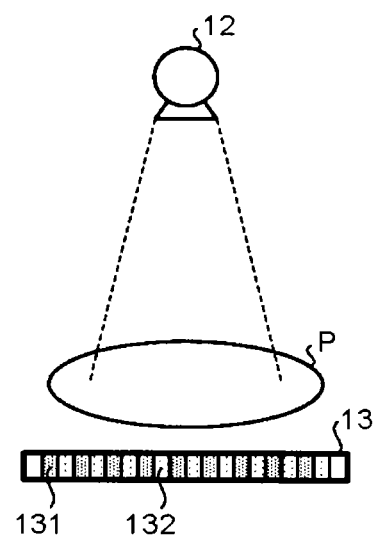

In the detector 13 according to the second embodiment, the plurality of first elements 131 structuring the first element group and the plurality of second elements 132 structuring the second element group are two-dimensionally arranged in a distributed manner. FIGS. 8A and 8B are drawings for explaining an example of the detector according to the second embodiment. For example, as illustrated in FIG. 8A, the plurality of first elements 131 and the plurality of second elements 132 are both arranged in rows of elements extending along the body-axis direction within the detector 13. In this situation, as illustrated in FIG. 8A, the rows of the plurality of first elements 131 and the rows of the plurality of second elements 132 are arranged so as to alternate along the channel direction.

With this arrangement in the second embodiment, it is possible to perform the first scan and the second scan while the relative positions of the X-ray tube 12 and the detector 13 are being fixed, as illustrated in FIG. 8B. In other words, according to the second embodiment, it is possible to perform the first scan and the second scan without the need to install the moving mechanism for the detector 13, which is required in the first embodiment.

In the second embodiment, as long as it is possible to fix the position of the detector 13 relative to the X-ray tube 12 for when performing the first scan and when performing the second scan, it is possible to configure the detector 13 in various styles. For example, it is possible to configure the second embodiment in such a manner that the plurality of first elements 131 and the plurality of second elements 132 are both arranged in rows of elements extending along the channel direction, while the rows of the plurality of first elements 131 and the rows of the plurality of second elements 132 are arranged so as to alternate along the body-axis direction. Alternatively, it is also acceptable to configure the second embodiment in such a manner that, for example, the plurality of first elements 131 and the plurality of second elements 132 are arranged so as to alternate in both the channel direction and the body-axis direction.

However, it should be noted that, when the rows of the first elements 131 and the rows of the second elements 132 are arranged so as to alternate, for example, it is desirable to arrange the rows of the first elements 131 to be as narrow as possible, for the purpose of preventing the spatial resolution of the X-ray image data acquired in the second scan from being degraded. Alternatively, for example, when the rows of the first elements 131 and the rows of the second elements 132 are arranged so as to alternate in both the channel direction and the body-axis direction, it is desirable to keep the size of the first elements 131 as small as possible, for the purpose of preventing the spatial resolution from being degraded.

Except for the configuration of the detector 13 where it is possible to fix the position of the detector 13 relative to the X-ray tube 12 for when performing the first scan and when performing the second scan, the explanation of the other configurations of the first embodiment is also applicable to the second embodiment.

Third Embodiment

Figure 9:
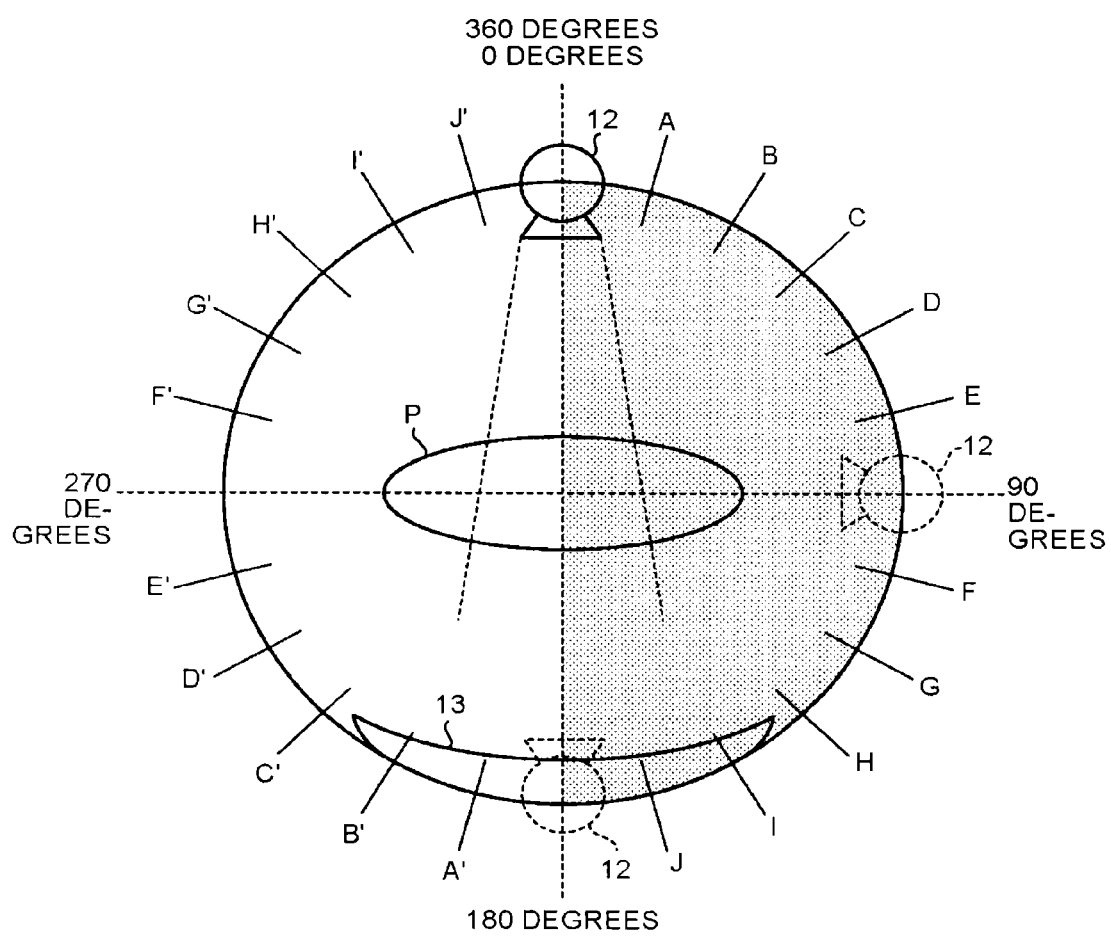
FIG. 9 is a drawing for explaining a first scan according to a third embodiment.

In a third embodiment, an example in which a controlling process is performed to reduce the exposure to the X-ray radiation during the first scan will be explained, with reference to FIG. 9. FIG. 9 is a drawing for explaining the first scan according to the third embodiment.

Figure 1C:
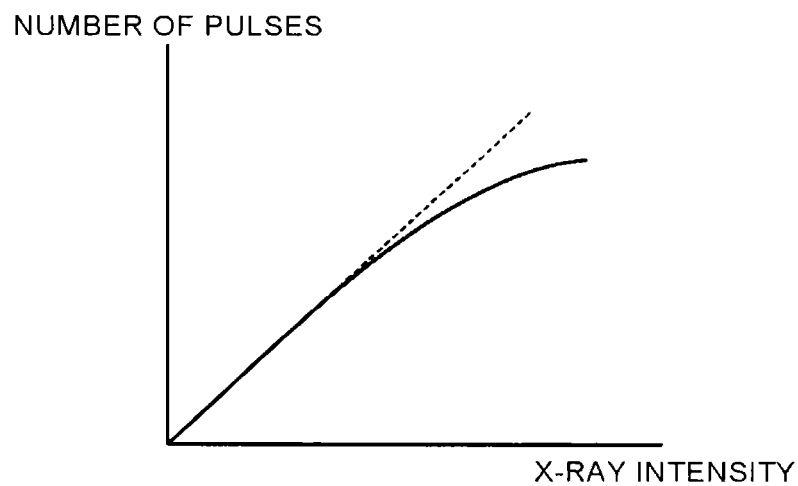

Although an X-ray CT apparatus according to the third embodiment is configured similarly to the X-ray CT apparatus according to the first embodiment explained with reference to FIG. 1, the first scan performed under the control of the scan controlling unit 33 is different from the first scan in the first embodiment. The first scan performed in the third embodiment will be explained below.

The scan controlling unit 33 according to the third embodiment causes the first scan to be performed with X-ray radiation half around the subject P. Specifically, as illustrated in FIG. 9, the scan controlling unit 33 causes the X-ray radiation to be emitted only in the range "from 0 to 180 degrees". In other words, the first scan performed in the third embodiment is a half scan.

Further, the scan controlling unit 33 according to the third embodiment obtains intensity distribution data corresponding to all around the subject by using the intensity distribution data of each of the X-ray tube phases corresponding to the half around the subject acquired in the first scan, as intensity distribution data of each of the respective opposite X-ray tube phases. In other words, the scan controlling unit 33 obtains the intensity distribution data corresponding to the range "from 180 to 360 degrees", by re-arranging the intensity distribution data corresponding to the range "from 0 to 180 degrees" into geometric positions that are in rotational symmetry centered on the rotation center of the rotating frame 15. After that, on the basis of the obtained intensity distribution data corresponding to all around the subject, the scan controlling unit 33 according to the third embodiment estimates an X-ray dose for each of the X-ray tube phases in which a counting result is to be acquired.

In this situation, for the purpose of further reducing the exposure to the X-ray radiation during the first scan, the scan controlling unit 33 according to the third embodiment causes the first scan to be performed with intermittently performing X-ray radiation around the subject P. In other words, the scan controlling unit 33 causes the first scan realized as a half scan to be performed with intermittent X-ray radiation (pulse-like X-ray radiation), instead of the continuous X-ray radiation. After that, the scan controlling unit 33 according to the third embodiment estimates intensity distribution data of such X-ray tube phases in which no intensity distribution data was acquired during the first scan by performing an interpolating process while using the intensity distribution data of such X-ray tube phases in which intensity distribution data has already been acquired.

For example, the scan controlling unit 33 causes pulse X-rays to be radiated at the angles of "0 degrees, A, B, C, D, E, 90 degrees, F, G, H, I, J, and 180 degrees" illustrated in FIG. 9. As a result, the intensity distribution data acquiring unit 14a acquires intensity distribution data corresponding to "0 degrees, A, B, C, D, E, 90 degrees, F, G, H, I, J, and 180 degrees" and transmits the acquired intensity distribution data to the scan controlling unit 33. Further, the scan controlling unit 33 determines that the intensity distribution data corresponding to "A, B, C, D, E, 90 degrees, F, G, H, I, and J" to be used as the intensity distribution data corresponding to "A', B', C', D', E', 270 degrees, F', G', H', I', and J'" illustrated in FIG. 9.

After that, for example, the scan controlling unit 33 estimates the intensity distribution data of the X-ray tube phase between "0 degrees" and "A" by performing an interpolating process while using the intensity distribution data corresponding to "0 degrees" and the intensity distribution data corresponding to "A". In this manner, the scan controlling unit 33 obtains the intensity distribution data corresponding to the range "from 0 degrees to 180 degrees". Further, for example, the scan controlling unit 33 determines that estimated intensity distribution data corresponding to "5 degrees" to be used as the intensity distribution data corresponding to "185 degrees". In this manner, the scan controlling unit 33 obtains the intensity distribution data corresponding to the range "from 180 degrees to 360 degrees".

After that, the scan controlling unit 33 estimates an optimal X-ray dose for each of the X-ray tube phases and causes the second scan to be performed.

Except that the method for performing the first scan is different, the explanations of the other configurations of the first and the second embodiments are also applicable to the third embodiment.

As explained above, in the third embodiment, on the premise that the X-ray intensities in the opposite positions are substantially equal as long as the X-ray transmission paths are the same, the first scan is performed as the half scan. Consequently, according to the third embodiment, it is possible to reduce the exposure to the X-ray radiation caused by the first scan. Further, in the third embodiment, the first scan is performed as the intermittent scan on the premise that it is possible to estimate the intensity distribution data of such X-ray tube phases in which no intensity distribution data was acquired, by performing the interpolating process while using the intensity distribution data acquired in the X-ray tube phases positioned before and after the X-ray tube phases in which no intensity distribution data was acquired. Consequently, according to the third embodiment, it is possible to further reduce the exposure to the X-ray radiation caused by the first scan.

Alternatively, it is also acceptable to configure the third embodiment in such a manner that the first scan realized as a half scan is performed with continuous X-ray radiation. Alternatively, it is also acceptable to configure the third embodiment in such a manner that the first scan is performed as a full scan realized with pulse X-ray radiation. In either situation, it is possible to reduce the exposure to the X-ray radiation compared to the situation where a full scan is performed with continuous X-ray radiation.

Further, it is acceptable to configure any of the first to the third embodiments in such a manner that, when a photon counting CT examination is performed in the same site of the same subject a plurality of times in a short time, the second scan is performed by conveniently using the optimal X-ray dose estimated from the intensity distribution data acquired in the previous first scan. In that situation, it is possible to perform the second scan while lowering the possibility of the occurrence of a pile-up without the first scan. It is therefore possible to significantly reduce the exposure to the X-ray radiation.

Further, as explained below, for the purpose of enlarging the dynamic range of the photon counting sensors, it is also acceptable to configure any of the first to the third embodiments by applying the modification example described below to the second element group served as the plurality of photon counting sensors. In the present modification example, the second element group is structured by using a plurality of types of elements having mutually-different levels of sensitivity to X-ray doses.

Figure 11:
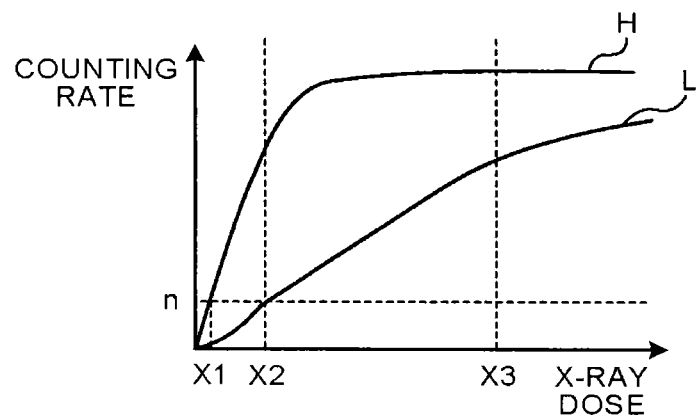

In this situation, the "levels of sensitivity to X-ray doses" means "counting rate characteristics with respect to X-ray doses". In other words, the second element group included in the detector 13 according to the present modification example is structured by using "the plurality of types of detecting elements of which the number of output electric signals per unit time are different, even if the same X-ray dose is incident thereto". In the following sections, an example will be explained in which the second element group is structured by using two types of second detecting elements (high-sensitivity elements and low-sensitivity elements) having mutually-different levels of sensitivity to the X-ray doses. The present modification example, however, is also applicable to a situation where the second element group is structured by using three or more types of second detecting elements having mutually-different levels of sensitivity to the X-ray doses. FIGS. 10 and 11 are drawings for explaining the modification example.

FIG. 10 illustrates an example in which the present modification example is applied to the detector 13 explained in the first embodiment. As illustrated in FIG. 10, the detector 13 according to the present modification example is divided into the first area 133 and the second area 134 along the channel direction, in the same manner as in the first embodiment described above. Further, as illustrated in FIG. 10, the plurality of first elements 131 configured with IS-purpose photodiodes are two-dimensionally arranged in the first area 133, in the same manner as in the first embodiment. Further, as illustrated in FIG. 10, in the present modification example, a plurality of low-sensitivity elements 132L and a plurality of high-sensitivity elements 132H that serve as PCS-purpose photon counting sensors are two-dimensionally arranged in the second area 134 so as to alternate.

By structuring the second element group in this manner, by combining the plurality of low-sensitivity elements 132L and the plurality of high-sensitivity elements 132H having the mutually-different levels of sensitivity to the X-ray doses, it is possible to obtain signal outputs having a larger dynamic range with respect to the X-ray doses. The curve H illustrated in FIG. 11 expresses response characteristics of the counting rate of the plurality of high-sensitivity elements 132H with respect to the X-ray doses. The curve L illustrated in FIG. 11 expresses response characteristics of the counting rate of the plurality of low-sensitivity elements 132L with respect to the X-ray doses. The "n" in FIG. 11 expresses a counting rate corresponding to noise.

When the curve H is compared with the curve L in FIG. 11, the X-ray dose "X1" with which the plurality of high-sensitivity elements 132H exhibit a counting rate corresponding to the noise level is smaller than the X-ray dose "X2" with which the plurality of low-sensitivity elements 132L exhibit a counting rate corresponding to the noise level. Further, the curve H in FIG. 11 indicates that, when the X-ray dose exceeds X2, miscounts for the number of photons occur in the plurality of high-sensitivity elements 132H due to a pile-up. In contrast, the curve L in FIG. 11 indicates that, when the X-ray dose exceeds X3, miscounts for the number of photons occur in the plurality of low-sensitivity elements 132L due to a pile-up.

Further, the curve H in FIG. 11 indicates that, for example, the counting rate characteristics of the plurality of high-sensitivity elements 132H are substantially linear in the range "X1 to X2". In other words, if the second element group was structured by using only the plurality of high-sensitivity elements 132H, the dynamic range would be "X1 to X2". In contrast, the curve L in FIG. 11 indicates that, for example, the counting rate characteristics of the plurality of low-sensitivity elements 132L are substantially linear in the range "X2 to X3". In other words, if the second element group was structured by using only the plurality of low-sensitivity elements 132L, the dynamic range would be "X2 to X3".

In the present modification example, however, because the second element group is structured by using the high-sensitivity elements 132H and the low-sensitivity elements 132L, the dynamic range of the detector 13 in a PCS is "X1 to X3", which is wider. In other words, according to the present modification example, the detector 13 is configured so as to have a larger dynamic range with which it is possible to reduce the occurrence of the pile-up, by structuring the second element group by using the plurality of types of elements having the mutually-different levels of sensitivity to the X-ray doses. The present modification example is also applicable to the detector 13 according to the second embodiment illustrated in FIG. 8A.

Further, in the present modification example, the scan controlling unit 33 estimates a PCS-purpose optimal X-ray dose on the basis of the intensity distribution data obtained in the IS. For example, in the present modification example, the scan controlling unit 33 estimates an optimal X-ray dose for each of the X-ray tube phases, by using "X3", for instance, as "Ith" explained in the first embodiment. The IS performed in the present modification example may be the IS explained in the first embodiment or may be the IS explained in the third embodiment.

In this situation, when X-ray CT image data is to be reconstructed in the modification example, the counting result acquiring unit 14b corrects one or both of the counted value (the counting rate) obtained from the high-sensitivity elements 132H and the counted value (the counting rate) obtained from the low-sensitivity elements 132L, so as to be a counted value (a counting rate) at the same level of sensitivity. The correcting process is performed on the basis of the shape of the curve H and the shape of the curve L, for example.

In the following explanation, the slope of the curve H in the range "X2 to X3" will be expressed as "dH", whereas the slope of the curve L in the range "X1 to X2" will be expressed as "dL". For example, the counting result acquiring unit 14b corrects the counted value obtained from the low-sensitivity elements 132L so as to be a counted value at a high-sensitivity level, by multiplying the counted value by "dH/dL". Alternatively, for example, the counting result acquiring unit 14b corrects the counted value obtained from the high-sensitivity elements 132H so as to be a counted value at a low-sensitivity level, by multiplying the counted value by "dL/dH".

The correcting process described above is merely an example. The correcting process described above may be performed by implementing another method by which, for example, a true counted value is statistically estimated on the basis of a counted value obtained when a pile-up has occurred. Further, the correcting process described above may be performed together with an interpolating process. For example, when performing a PCS in the range "X1 to X2", the counting result acquiring unit 14b may estimate counted values in the locations where the low-sensitivity elements 132L are positioned, by performing an interpolating process while using the counted values obtained from the high-sensitivity elements 132H that are positioned in the surroundings of the low-sensitivity elements 132L. Further, when performing a PCS in the range "X2 to X3", the counting result acquiring unit 14b may estimate counted values of the high-sensitivity elements 132H, by performing an interpolating process while using the counted values obtained from the low-sensitivity elements 132L that are positioned in the surroundings of the high-sensitivity elements 132H. After that, the counting result acquiring unit 14b corrects the estimated values obtained from the interpolating processes so as to be values at the same level of sensitivity. Alternatively, the various correcting processes performed on the counted values in the present modification example may be performed by the gantry device 10 or by the console device 30.

As explained above, according to the present modification example, it is possible to further reduce the occurrence of miscounts by structuring the second element group by using the plurality of types of elements having the mutually-different levels of sensitivity to the X-ray doses.

The controlling methods explained in any of the first to the third embodiments and the modified examples may be realized by causing a computer such as a personal computer or a workstation to execute a controlling computer program (hereinafter, a "controlling program") that is prepared in advance. The controlling program may be distributed via a network such as the Internet. Further, it is also possible to record the controlling program onto a computer-readable recording medium such as a hard disk, a flexible disk (FD), a Compact Disk Read-Only Memory (CD-ROM), a Magneto-optical (MO) disk, a Digital Versatile Disk (DVD), or the like, so that a computer is able to read the controlling program from the recording medium and to execute the read program.

As explained above, according to at least one aspect of the first to the third embodiments and the modified examples, it is possible to reduce the occurrence of miscounts.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
an X-ray tube;
a detector including a first element group that detects an X-ray intensity and a second element group that counts X-ray photons;
intensity distribution data acquiring circuitry configured to acquire, by performing a first scan, intensity distribution data of X-rays that are radiated from the X-ray tube and that have passed through a subject;
scan controlling circuitry configured to estimate an X-ray dose with which it is possible to discriminate individual X-ray photons that have passed through the subject based on the intensity distribution data, and to cause a second scan that is for a photon counting CT purpose to be performed by causing the estimated X-ray dose to be radiated from the X-ray tube to the subject;
counting result acquiring circuitry configured to acquire, by the second scan, a counting result by counting the X-ray photons that are radiated from the X-ray tube and that have passed through the subject; and
image reconstructing circuitry configured to reconstruct X-ray CT image data based on the counting result, wherein
the detector is divided into a first area and a second area along a channel direction, so that the first element group is arranged in the first area, whereas the second element group is arranged in the second area, and
the scan controlling circuitry is further configured to exercise control so as to move the first area to a position facing the X-ray tube when performing the first scan and to move the second area to a position facing the X-ray tube when performing the second scan, and is configured to cause the first scan to be performed by employing the first element group and to cause the second scan to be performed by employing the second element group.

2. The X-ray CT apparatus according to claim 1, wherein the scan controlling circuitry is further configured to cause the first scan to be performed with performing X-ray radiation all around the subject and to estimate the X-ray dose for each of X-ray tube phases in which the counting result is acquired, based on the intensity distribution data corresponding to all around the subject acquired in the first scan.

3. The X-ray CT apparatus according to claim 2, wherein the scan controlling circuitry is further configured to cause the first scan to be performed with intermittently performing X-ray radiation around the subject, and to estimate intensity distribution data of the X-ray tube phases in which no intensity distribution data was acquired during the first scan, by performing an interpolating process while using intensity distribution data of the X-ray tube phases in which intensity distribution data has already been acquired.

4. The X-ray CT apparatus according to claim 1, wherein the scan controlling circuitry is further configured to cause the first scan to be performed with performing X-ray radiation half-way around the subject, obtain intensity distribution data corresponding to all around the subject by using intensity distribution data of each of X-ray tube phases corresponding to the half-way around the subject acquired in the first scan, as intensity distribution data of opposite X-ray tube phases, and to estimate the X-ray dose for each of X-ray tube phases in which the counting result is acquired, based on the obtained intensity distribution data corresponding to all around the subject.

5. The X-ray CT apparatus according to claim 4, wherein the scan controlling circuitry is further configured to cause the first scan to be performed with intermittently performing X-ray radiation around the subject and to estimate intensity distribution data of the X-ray tube phases in which no intensity distribution data was acquired during the first scan, by performing an interpolating process while using intensity distribution data of the X-ray tube phases in which intensity distribution data has already been acquired.

6. The X-ray CT apparatus according to claim 1, wherein the scan controlling circuitry is further configured to cause the first scan and the second scan, once each, to be performed alternately and successively on a same trajectory.

7. The X-ray CT apparatus according to claim 1, wherein the second element group includes a plurality of types of elements having mutually-different levels of sensitivity to X-ray doses.

8. The X-ray CT apparatus according to claim 1, wherein the scan controlling circuitry is further configured to suspend data output from the counting result acquiring circuitry when performing the first scan and suspend data output from the intensity distribution data acquiring circuitry when performing the second scan.

9. An X-ray CT apparatus, comprising:
an X-ray tube;
a detector including a first element group that detects an X-ray intensity and a second element group that counts X-ray photons;
intensity distribution data acquiring circuitry configured to acquire, by performing a first scan, intensity distribution data of X-rays that are radiated from the X-ray tube and that have passed through a subject;
scan controlling circuitry configured to estimate an X-ray dose with which it is possible to discriminate individual X-ray photons that have passed through the subject based on the intensity distribution data, and to cause a second scan that is for a photon counting CT purpose to be performed by causing the estimated X-ray dose to be radiated from the X-ray tube to the subject;
counting result acquiring circuitry configured to acquire, by the second scan, a counting result by counting the X-ray photons that are radiated from the X-ray tube and that have passed through the subject; and
image reconstructing circuitry configured to reconstruct X-ray CT image data based on the counting result, wherein
in the detector, the first element group includes a plurality of first elements and the second element group includes a plurality of second elements, the plurality of first elements and the plurality of second elements being arranged alternately along any one of a channel direction and a body-axis direction, and the scan controlling circuitry is further configured to cause the first scan to be performed by employing the first element group and to cause the second scan to be performed by employing the second element group.

10. The X-ray CT apparatus according to claim 9, wherein the scan controlling circuitry is further configured to cause the first scan to be performed with performing X-ray radiation all around the subject and to estimate the X-ray dose for each of X-ray tube phases in which the counting result is acquired, based on the intensity distribution data corresponding to all around the subject acquired in the first scan.

11. The X-ray CT apparatus according to claim 10, wherein the scan controlling circuitry is further configured to cause the first scan to be performed with intermittently performing X-ray radiation around the subject, and to estimate intensity distribution data of the X-ray tube phases in which no intensity distribution data was acquired during the first scan, by performing an interpolating process while using intensity distribution data of the X-ray tube phases in which intensity distribution data has already been acquired.

12. The X-ray CT apparatus according to claim 9, wherein the scan controlling circuitry is further configured to cause the first scan to be performed with performing X-ray radiation half-way around the subject, obtain intensity distribution data corresponding to all around the subject by using intensity distribution data of each of X-ray tube phases corresponding to the half-way around the subject acquired in the first scan, as intensity distribution data of opposite X-ray tube phases, and to estimate the X-ray dose for each of X-ray tube phases in which the counting result is acquired, based on the obtained intensity distribution data corresponding to all around the subject.

13. The X-ray CT apparatus according to claim 12, wherein the scan controlling circuitry is further configured to cause the first scan to be performed with intermittently performing X-ray radiation around the subject and to estimate intensity distribution data of the X-ray tube phases in which no intensity distribution data was acquired during the first scan, by performing an interpolating process while using intensity distribution data of the X-ray tube phases in which intensity distribution data has already been acquired.

14. The X-ray CT apparatus according to claim 9, wherein the scan controlling circuitry is further configured to cause the first scan and the second scan, once each, to be performed alternately and successively on a same trajectory.

15. The X-ray CT apparatus according to claim 9, wherein the second element group includes a plurality of types of elements having mutually-different levels of sensitivity to X-ray doses.

16. The X-ray CT apparatus according to claim 9, wherein the scan controlling circuitry is further configured to suspend data output from the counting result acquiring circuitry when performing the first scan and suspend data output from the intensity distribution data acquiring circuitry when performing the second scan.

17. An X-ray CT apparatus, comprising:
an X-ray tube;
intensity distribution data acquiring circuitry configured to acquire, by performing a first scan, intensity distribution data of X-rays that are radiated from the X-ray tube and that have passed through a subject;
scan controlling circuitry configured to estimate an X-ray dose with which it is possible to discriminate individual X-ray photons that have passed through the subject based on the intensity distribution data, and to cause a second scan that is for a photon counting CT purpose to be performed by causing the estimated X-ray dose to be radiated from the X-ray tube to the subject;
counting result acquiring circuitry configured to acquire, by the second scan, a counting result by counting the X-ray photons that are radiated from the X-ray tube and that have passed through the subject; and
image reconstructing circuitry configured to reconstruct X-ray CT image data based on the counting result,
the scan controlling circuitry is further configured to suspend data output from the counting result acquiring circuitry when performing the first scan and suspend data output from the intensity distribution data acquiring circuitry when performing the second scan.

18. A controlling method, comprising:
acquiring, by performing a first scan using a detector including a first element group that detects an X-ray intensity and a second element group that counts X-ray photons, intensity distribution data of X-rays that are radiated from an X-ray tube and that have passed through a subject;
estimating, by scan controlling circuitry, an X-ray dose with which it is possible to discriminate individual X-ray photons that have passed through the subject based on the intensity distribution data and causing a second scan that is for a photon counting CT purpose to be performed by causing the estimated X-ray dose to be radiated from the X-ray tube to the subject;
acquiring, by the second scan, a counting result by counting the X-ray photons that are radiated from the X-ray tube and that have passed through the subject;
reconstructing X-ray CT image data based on the counting result, wherein the detector is divided into a first area and a second area along a channel direction, so that the first element group is arranged in the first area, whereas the second element group is arranged in the second area; and
exercising control, by the scan controlling circuitry, so as to move the first area to a position facing the X ray tube when performing the first scan and to move the second area to a position facing the X-ray tube when performing the second scan, and causing the first scan to be performed by employing the first element group and causing the second scan to be performed by employing the second element group.

* * * * *